United States Patent [19]

Park et al.

[11] Patent Number: 5,571,909
[45] Date of Patent: Nov. 5, 1996

[54] CEPHALOSPORIN COMPOUNDS AND PROCESSES FOR PREPARING THEREOF

[75] Inventors: Hokoon Park; Sun Ho Jung; Yong Sup Lee; Jae Yeol Lee; Eun-Rhan Woo, all of Seoul, Rep. of Korea

[73] Assignee: Korea Institute of Science and Technology, Seoul, Rep. of Korea

[21] Appl. No.: 255,266

[22] Filed: Jun. 7, 1994

[30] Foreign Application Priority Data

Jun. 9, 1993 [KR] Rep. of Korea .................. 10422/1993

[51] Int. Cl.$^6$ ................................................. C07D 501/38
[52] U.S. Cl. ........................................................ 540/222
[58] Field of Search ............................. 540/222; 514/202

[56] References Cited

U.S. PATENT DOCUMENTS 5,010,188   4/1991   Yamauchi et al. ...................... 540/222
5,366,970   11/1994  Sakine et al. ............................ 514/202

FOREIGN PATENT DOCUMENTS 57-126492   8/1982   Japan .

OTHER PUBLICATIONS

*Drugs of the Future*, vol. 13(4), pp. 369–371 (1988).
*Drugs of the Future*, vol. 13(10), pp. 805–808 (corresponding to DE Pat. No. 3,307,550).
*Synthesis and Structure–Activity Relationships of a New Series of Cephalosporins, BMY–28142 and Related Compounds*, The Journal of Antibiotics, 39(8), pp. 1092–1107.

*Primary Examiner*—John M. Ford
*Assistant Examiner*—Pavanaram K. Sripada
*Attorney, Agent, or Firm*—Darby & Darby, P.C.

[57] ABSTRACT

Quaternary ammoniocephalosporins of formula(I) wherein Q=CH or N, P=hydroxylated amine or hydroxylated heterocyclylamines including N-methyl-bis(2-hydroxyethyl)amine, rac-3,4-trans-dihydroxy-1-methylpyrrolidine, (3S, 4S)-3,4-dihydroxy-1-methylpyrrolidine, (3R,4R)-3,4-dihydroxy-1-methylpyrrolidine, meso-3,4-dihydorcy-1-methylpyrrolidine, (2S, 4R)-4-hydroxy-1-methyl-2-pyrrolidinemethanol 3,4-cis-dihydroxy-1-methylpiperidine, 3,4-trans-dihydroxy-1-methylpiperidine, or tropine, and preparation methods are disclosed.

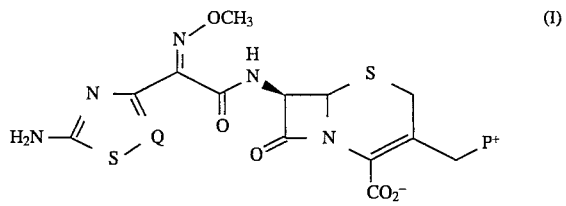

(I)

3 Claims, No Drawings

CEPHALOSPORIN COMPOUNDS AND PROCESSES FOR PREPARING THEREOF

BACKGROUND OF THE INVENTION

1. Field of the Invention

The present invention relates to novel quaternary ammoniocephalosporins with hydroxylated alicyclic or aliphatic amines of the general formula (I)

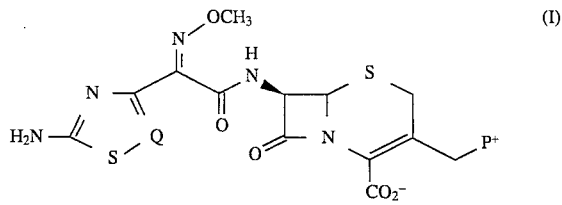

as useful antibacterial agents and the preparation method thereof. In the formula(I), Q=CH or N, P= hydroxylated amine or hydroxylated heterocyclylamines including N-methyl-bis(2-hydroxyethyl)amine, rac-3,4-trans-dihydroxy-1-methylpyrrolidine, (3S, 4S)-3,4-dihydroxy-1-methylpyrrolidine, (3R,4R)-3,4-dihydroxy-1-methylpyrrolidine, meso-3,4-dihydorcy-1-methylpyrrolidine, (2S, 4R)-4-hydroxy-1-methyl-2-pyrrolidinemethanol 3,4-cis-dihydroxy-1-methylpiperidine, 3,4-trans-dihydroxy-1-methylpiperidine, or tropine.

2. Description of the Prior Art

Belgium Pat. No. 876,538 describes the preparation of pyridiniomethyl cephalosporin (ceftazidime), which show broad and potent antibacterial activities. However, it is less active aganist Staphylococci and *Enterobacter cloacae* P99. Thereafter many quaternary ammoniomethyl cephalosporin derivatives such as cefpirome (Drugs of the Future, 13, 369–371 (1988)) and cefepime (Ger. Pat. No. 3,307,550) were developed. Cefpirome is prepared by the reaction of cefotaxime with 2,3-cyclopentenopyridine in the presence of N-methyl-N-(trimethylsilyl)trifluoroactamide or trmethylsilyl iodide. Cefepime is a aminothizolyl cephalosporin derivative having a aliphatic ammonium group at C-3 position and prepared from 7-ACA and 1-methylpyrrolidine. The detailed synthesis of cefepime is described in Journal of Antibiotics, 1986, 39(8), 1092–1107. Cefpirome and cefepime exhibit improved anti-staphylococcal activity while retaining high anti-pseudomonal activity.

SUMMARY OF THE INVENTION

The present invention relates to novel quaternary ammoniocephalosporins with hydroxylated alicyclic or aliphatic amines as useful antibacterial agents and the preparation method thereof.

DETAILED DESCRIPTION OF THE PREFFERRED EMBODIMENTS

In accordance with the present invention, there are provided new quaternary ammonium cephalosporins represented as formula (I) having a quaternary hydroxylated alicyclic or aliphatic amines exhibiting potent antibacterial activities against Gram-positive and Gram-negative strains including *Streptococcus pyogenes* 308A, *Escherichia coli*, TEM, *Pseudomonas aeruginosa* 9027, and *Enterobacter cloacae* P99 etc.

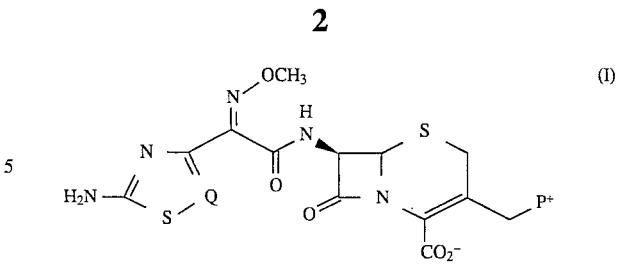

In formula (I), Q=CH or N, P=hydroxylated amine or hydroxylated heterocyclylamines including N-methyl-bis(2-hydroxyethyl)amine, rac-3,4-trans-dihydroxy-1-methylpyrrolidine, (3S, 4S)-3,4-dihydroxy-1-methylpyrrolidine, (3R, 4R)-3,4-dihydroxy-1-methylpyrrolidine, meso-3,4-dihydroxy-1-methylpyrrolidine, (2S, 4R)-4-hydroxy-1-methyl-2-pyrrolidinemethanol, 3,4-cis-dihydroxy-1-methylpiperidine, 3,4-trans-dihydroxy-1-methylpiperidine, or tropine.

In accordance with the present invention, there is also provided a method for preparation of the quaternary ammonium cephalosporins represented as formula I which comprises a quaternization of 7-amino-3-(iodomethyl)-3-cephem-4-carboxylic acid (iodomethylcephem) represented as the formula (II) with hydroxylated alicyclic or aliphatic amine represented as formula (III) followed by in situ acylation with aminothiazole hydroxybenzothiazole active ester in one-pot procedure.

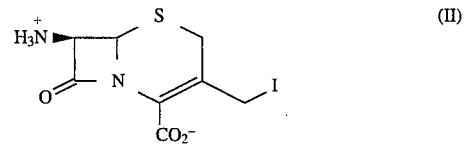

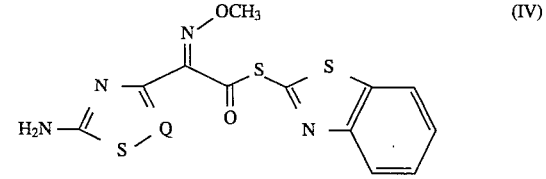

The iodomethylcephem of the formula (II) can be prepared according to the method described in Japanese Pat. No. 126,492.

In the general formula (III), P represents tertiary amine such as N-methyl-bis(2-hydroxyethyl)amine, rac-3,4 -trans-dihydroxy-1-methylpyrrolidine, (3S, 4S)-3,4-dihydroxy-1-methyl-pyrrolidine, (3R, 4R)-3,4-dihydroxy-1-methylpyrrolidine, meso-3,4-methyl-pyrrolidine, (2S, 4R)-4-hydroxy-1-methyl-2-pyrrolidinemethanol, 3,4-cis-dihydroxy-1-methyl-piperidine, 3,4-trans-dihydroxy-1-methylpiperidine, or tropine.

N-methyl-bis(2-hydroxyethyl)amine and tropine are commercially available from Aldrich Co. Ltd.

Rac-3,4-trans-Dihydroxy-1-methylpyrrolidine, (3S, 4S)-3,4-dihydroxy-1-methylpyrrolidine, (3R, 4R)-3,4-dihydroxy-1-methylpyrrolidine, meso-3,4-dihydroxy-1-methylpyrrolidine, and (2S, 4R)-4-hydroxy-1-methyl-2-pyrrolidinemethanol are new compounds and their preparations were described in detail in examples.

In the formula (IV), Q represents CH or N and can be prepared according to the method described in Austrian AT 387,022, Nov. 25, 1988.

The new cephalosporin represented as formula I can be prepared as follows: The iodomethyl cephera (II) is quaternized with 1–10 equivalents, preferably 3 equivalents of tertiary amine of the general formula (III) and 1–12 hours stirring followed by addition of 0.5–3 equivalents, preferably 1.2 equivalents of active ester (IV) and additional 2–12 hours stirring to obtain crude cephalosporin represented as formula (I). The crude cephalosporins (I) may be purified by silica gel column chromatography using acetonitrile-water(4:1) as an eluent and freeze drying.

The used solvent in this reaction is a polar solvent, preferably aqueous or anhydrous N,N-dimethylformamide (DMF).

exhibited higher activity against *Enterobacter cloacae* P99, which is resistant to ceftazidime.

The activities of aminothiadiazolyl derivatives of the general formula I (Q=N) are shown in Table 2. They exhibit better activity than ceftazidime against Gram-positive and Gram-negative organisms. The replacement of aminothiazole moiety to aminothiadiazole moiety causes somewhat increase of anti-pseudomonal activities and somewhat

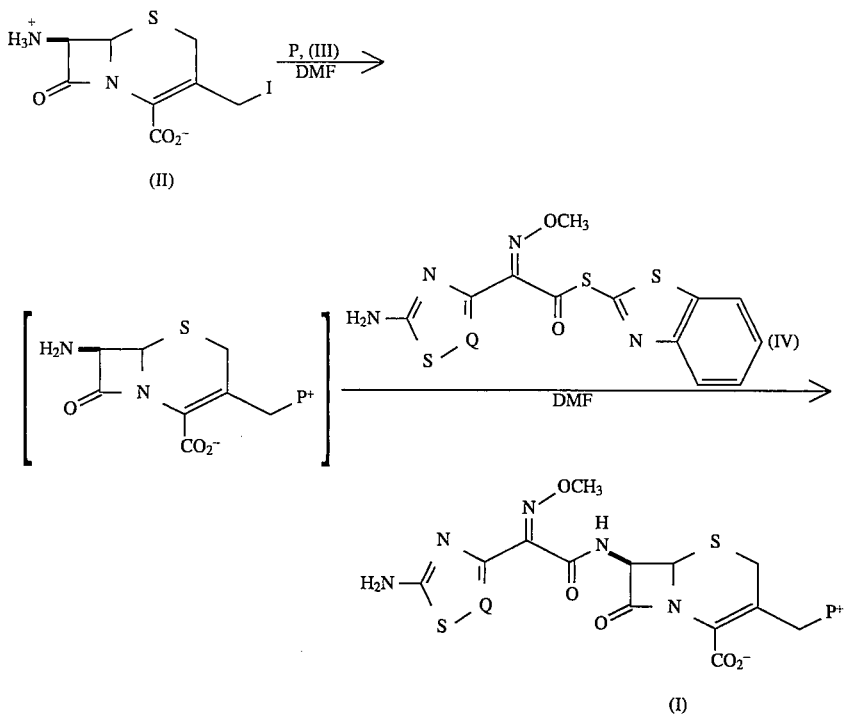

The Minimum Inhibitory Concentration (MIC) values of the new cephalosporins of the present invention against Gram-positive and Gram-negative bacteria were determined by an in vitro agar dilution method and the results are listed in table 1. For comparisons, the MIC values of ceftazidime are also listed.

The cephalosporins of the present invention exhibited broad and potent antibacterial activities against Gram-positive and Gram-negative bacterias.

Table 1 shows in vitro activities of the aminothiazolyl derivatives of cephalosporins of the present invention(Q=CH). The activities of the most of the compounds are similar to each other. Aminothiadiazolyl derivatives show somewhat better activities than ceftazidime against Gram-positive organisms. The anti-pseudomonal activities of them are comparable to ceftazidime. Especially, they decrease of anti-staphylococcal activity. Aminothiadiazolyl derivatives also exhibit high activity against enterobacter cloacae P99.

In order to examine the effect of the stereochemistry of the hydroxy group, the antibacterial activities of cephalosporins quaternised with three optical isomers of 1-methyl-3,4-trans-dihydroxypyrrolidines were investigated. The necessary heterocycles were obtained from L-, D- and racemic tartaric acid respectively. The activities of them were nearly the same as each other, there being no relationship of activity with the stereochemistry of the hydroxy group.

According to these results, hydroxylated aliphatic and alicyclic ammonium cephalosporins represented as formula (I) are found to be more active than ceftazidime.

The examples which follows and which are given without implying a limitation show how the invention can be put into practice.

TABLE 1

| Strains | I-a | I-b | I-c | I-d | I-e | I-f | I-g | I-h | I-i | Ceftazidime |
|---|---|---|---|---|---|---|---|---|---|---|
| 1 *Streptococcus pygenenes* 308 A | 0.025 | 0.025 | 0.025 | 0.025 | 0.049 | 0.025 | 0.049 | 0.049 | 0.025 | 0.098 |
| 2 *Streptococcus pygenenes* 77 A | 0.013 | 0.025 | 0.007 | 0.013 | 0.025 | 0.025 | 0.025 | 0.025 | 0.013 | 0.049 |
| 3 *Streptococcus faecium* MD 8b | 100 | 100 | 50 | 100 | 100 | 50 | 100 | 100 | 100 | >100 |
| 4 *Streptococcus aureus* SG 511 | 6.25 | 6.25 | 3.125 | 3.125 | 6.25 | 3.125 | 6.25 | 6.25 | 3.125 | 12.5 |
| 5 *Streptococcus aureus* 285 | 12.5 | 12.5 | 6.25 | 12.5 | 25 | 6.25 | 12.5 | 12.5 | 12.5 | 12.5 |
| 6 *Streptococcus aureus* 503 | 3.125 | 1.563 | 1.563 | 1.563 | 3.125 | 1.563 | 3.125 | 3.125 | 1.563 | 3.125 |
| 7 *Eschorichia coli* 055 | 0.025 | 0.025 | 0.025 | 0.025 | 0.049 | 0.025 | 0.025 | 0.049 | 0.025 | 0.098 |
| 8 *Eschorichia coli* DC 0 | 0.098 | 0.049 | 0.09 | 0.049 | 0.098 | 0.049 | 0.098 | 0.098 | 0.098 | 0.098 |

TABLE 1-continued

| Strains | I-a | I-b | I-c | I-d | I-e | I-f | I-g | I-h | I-i | Cefta-zidime |
|---|---|---|---|---|---|---|---|---|---|---|
| 9 Eschorichia coli DC 2 | 0.049 | 0.049 | 0.049 | 0.049 | 0.098 | 0.049 | 0.049 | 0.098 | 0.049 | 0.098 |
| 10 Eschorichia coli TEM | 0.098 | 0.098 | 0.098 | 0.098 | 0.195 | 0.098 | 0.195 | 0.195 | 0.195 | 0.195 |
| 11 Eschorichia coli 1507 E | 0.098 | 0.049 | 0.049 | 0.049 | 0.098 | 0.098 | 0.049 | 0.098 | 0.098 | 0.195 |
| 12 Pseudomonas aeruginosa 9027 | 6.25 | 3.125 | 6.25 | 6.25 | 6.25 | 6.25 | 6.25 | 6.25 | 6.25 | 3.125 |
| 13 Pseudomonas aeruginosa 1592 E | 1.563 | 3.125 | 1.563 | 3.125 | 6.25 | 3.125 | 3.125 | 3.125 | 3.125 | 0.781 |
| 14 Pseudomonas aeruginosa 1771 | 0.195 | 0.781 | 0.781 | 0.781 | 0.781 | 0.781 | 1.563 | 1.563 | 3.125 | 0.391 |
| 15 Pseudomonas aeruginosa 1771 M | 0.098 | 0.049 | 0.195 | 0.195 | 0.098 | 0.098 | 0.098 | 0.195 | 0.195 | 0.098 |
| 16 Salmonella typhimurium | 0.049 | 0.049 | 0.098 | 0.049 | 0.098 | 0.049 | 0.049 | 0.098 | 0.098 | 0.195 |
| 17 Krebsiella oxyloca 1082 E | 3.125 | 1.563 | 1.563 | 3.125 | 0.098 | 1.563 | 1.563 | 1.563 | 3.125 | 0.391 |
| 18 Krebsiella aerogenes 1552 E | 0.049 | 0.025 | 0.049 | 0.025 | 0.049 | 0.049 | 0.049 | 0.049 | 0.098 | 0.098 |
| 19 Enterobacter cloacae P99 | 3.125 | 6.25 | 3.125 | 3.125 | 6.25 | 1.563 | 1.563 | 3.125 | 3.125 | 100 |
| 20 Enterobacter cloacae 1321 E | 0.013 | 0.013 | 0.007 | 0.013 | 0.025 | 0.013 | 0.025 | 0.025 | 0.025 | 0.025 |

TABLE 2

| Strains | I-j | I-k | I-l | I-m | I-n | I-o | I-p | I-q | I-r | Cefta-zidime |
|---|---|---|---|---|---|---|---|---|---|---|
| 1 Streptococcus pygenenes 308 A | 0.098 | 0.049 | 0.049 | 0.098 | 0.098 | 0.049 | 0.098 | 0.098 | 0.049 | 0.098 |
| 2 Streptococcus pygenenes 77 A | 0.098 | 0.049 | 0.049 | 0.049 | 0.09 | 0.049 | 0.049 | 0.049 | 0.025 | 0.049 |
| 3 Streptococcus faecium MD 8b | 100 | 100 | 100 | 100 | 100 | 100 | 100 | 100 | 100 | >100 |
| 4 Streptococcus aureus SG 511 | 12.5 | 6.25 | 6.25 | 6.25 | 6.25 | 6.25 | 6.25 | 6.25 | 3.125 | 12.5 |
| 5 Streptococcus aureus 285 | 25 | 12.5 | 12.5 | 12.5 | 12.5 | 12.5 | 12.5 | 12.5 | 6.25 | 12.5 |
| 6 Streptococcus aureus 503 | 6.25 | 6.25 | 3.125 | 6.25 | 3.125 | 3.125 | 3.125 | 3.125 | 1.563 | 3.125 |
| 7 Eschorichia coli 055 | 0.098 | 0.098 | 0.049 | 0.049 | 0.098 | 0.049 | 0.098 | 0.098 | 0.098 | 0.098 |
| 8 Eschorichia coli DC 0 | 0.098 | 0.098 | 0.049 | 0.098 | 0.195 | 0.098 | 0.098 | 0.098 | 0.195 | 0.098 |
| 9 Eschorichia coli DC 2 | 0.195 | 0.195 | 0.195 | 0.195 | 0.391 | 0.195 | 0.391 | 0.391 | 0.391 | 0.098 |
| 10 Eschorichia coli TEM | 0.098 | 0.195 | 0.195 | 0.195 | 0.391 | 0.195 | 0.195 | 0.195 | 0.391 | 0.195 |
| 11 Eschorichia coli 1507 E | 0.098 | 0.098 | 0.098 | 0.098 | 0.195 | 0.098 | 0.195 | 0.195 | 0.195 | 0.195 |
| 12 Pseudomonas aeruginosa 9027 | 1.563 | 1.563 | 1.563 | 3.125 | 1.563 | 1.563 | 1.563 | 1.563 | 1.563 | 3.125 |
| 13 Pseudomonas aeruginosa 1592 E | 1.563 | 1.563 | 0.781 | 1.563 | 0.781 | 1.563 | 1.563 | 0.781 | 1.563 | 0.781 |
| 14 Pseudomonas aeruginosa 1771 | 0.391 | 0.391 | 0.195 | 0.781 | 0.391 | 0.391 | 0.391 | 0.391 | 0.195 | 0.391 |
| 15 Pseudomonas aeruginosa 1771 M | 0.098 | 0.049 | 0.049 | 0.195 | 0.049 | 0.049 | 0.049 | 0.049 | 0.025 | 0.098 |
| 16 Salmonella typhimurium | 0.098 | 0.195 | 0.098 | 0.098 | 0.195 | 0.098 | 0.195 | 0.195 | 0.391 | 0.195 |
| 17 Krebsiella oxyloca 1082 E | 0.098 | 1.563 | 1.563 | 3.125 | 3.125 | 0.781 | 1.563 | 1.563 | 1.563 | 0.391 |
| 18 Krebsiella aerogenes 1552 E | 0.049 | 0.098 | 0.098 | 0.049 | 0.195 | 0.049 | 0.098 | 0.098 | 0.098 | 0.098 |
| 19 Enterobacter cloacae P99 | 1.563 | 3.125 | 3.125 | 1.563 | 3.125 | 1.563 | 1.563 | 1.563 | 3.125 | 100 |
| 20 Enterobacter cloacae 1321 E | 0.049 | 0.049 | 0.025 | 0.025 | 0.049 | 0.025 | 0.049 | 0.09 | 0.098 | 0.025 |

EXAMPLE 1

To a solution of 3-pyrroline (1.3 g, 18.8 mmol) and anhyd. potassium carbonate (15.3 g, 144.6 mmol) in methylene chloride (30 mL) was added dropwise benzyl chloroformate (7.4 g, 43.4 mmol) at 0° C. and stirred for 20 min. The reaction mixture was warmed to room temperature and stirred further for 2 hrs. The mixture was washed with cold water (30 mL) and brine (20 mL) and dried (MgSO$_4$). After evaporation of solvents, the residue was purified by flash column chromatography (EtOAc/hexane (1:10)) to give 1-benzyloxycarbonyl-3-pyrroline (3 g, 78%). To a solution of catalytic amount of osmium tetroxide in water (15 mL) and acetone (7 ml) was added N-methylmorpholine 1H$_2$O (479 mg, 3.5 mmol) and 1-benzyloxycarbonyl-3-pyrroline (600 mg, 3.0 mmol), and stirred overnight. To the reaction mixture were added sodium hydrosulfite (0.1 g) and florisil (2 g) and stirred for 30 min. The reaction mixture was filtered and washed with acetone (10 mL×2). The combined organic solution was dried (MgSO$_4$), evaporated, and purified by flash column chromatography (EtOAc/hexane (1:1) -EtOAc only) to give meso-1-benzyloxycarbonyl-3,4-dihydroxypyrrolidine (586 mg, 84%) as an oil.

$^1$H-NMR (CDCl$_3$) δ7.36 (5H, s), 5.13 (2H, s), 4.25 (2 H, m), 3.65 (2H, dd, J=11 and 5 Hz), 3.44 (2H, dd, J=11 and 3 Hz). The solution of meso-1-benzyloxycarbonyl-3,4-dihydroxypyrrolidine (270 mg, 1.14 mmol) and 10% Pd/C (27 mg) in 95% ethanol (10mL) was stirred at room temperature for 6 hrs under hydrogen atmosphere (1 atm.). The reaction mixture was filtered through Celite-545 and the filtrate was concentrated at reduced pressure. The residue was diluted with 35% formaldehyde solution (4.5 mL) and formic acid (5.5 mL), and refluxed for 24 hrs. After evaporating the solvents, the residue was diluted with chloroform (10 mL) and filtered to remove insoluble materials. The filtrate was concentrated at reduced pressure to give meso-3,4-dihydroxy-1-methylpyrrolidine as an oil.

$^1$H-NMR (CDCl$_3$) δ4.17 (2H, m), 2.67 (4H, m), 2.30 (3H, m).

EXAMPLE 2

To a suspension of lithium aluminum hydride (1.24 g, 32.7 mmol) in THF (60 mL) was added a solution of rac-3,4-trans-diacetoxy-2,5-dioxo-1-methylpyrrolidine (1.5 g, 6.54 mmol) in THF (20 mL) dropwise at 0° C. for 30 min. After refluxing for 24 hrs, the reaction mixture was cooled to 0° C. and quenched by slow addition of ethyl acetate (2 mL), ethanol (15 mL), and water (10 mL) in turn. The mixture was warmed to room temperature and stirred vigorously for 30 min. The mixture was filtered through Celite-545 and washed with chloroform-ethanol (1:1, 20 mL×3).

The filtrate was concentrated at reduced pressure and Kugelrohr distilled to give a slightly yellow solid. Then, the solid was purified by recrystallization from chloroform-ethyl acetate afforded rac-3,4-trans-dihydroxy-1-methylpyrrolidine (427 mg, 57%) as a white needle. mp 93°–95° C.;

$^1$H-NMR (CDCl$_3$) δ4.79 (2H, br s), 4.10 (2H, m), 2.94 (2 H, dd, J=10 and 6 Hz), 232 (3H, s).

EXAMPLE 3

By the use of the procedure described above for rac-3,4-trans-dihydroxy-1-methylpyrrolidine, (3S, 4S)-3,4-dihydroxy-1-methylpyrrolidine was prepared from (3R, 4R)-3, 4-diacetoxy-1-methylpyrrolidine. mp 93°–95° C.; [α]$_D$=+28° (c 0.05, MeOH).

EXAMPLE 4

By the use of the procedure described above for (3S, 4S)-3,4-dihydroxy-1-methylpyrrolidine, (3R, 4R)-3,4-dihydroxy-1-methylpyrrolidine was prepared from (3S, 4S)-3,4-diacetoxy-1-methylpyrrolidine. mp 93°–95° C.; [α]$_D$=−28° (c 0.06, MeOH).

EXAMPLE 5

A 2-L three-necked, round-bottomed flask was equipped with a mechanical stirrer, heating mantel, 250-mL graduated additional funnel, and an 8-in., air-cooled vigreux column topped with a water-cooled distillation head and a 1-L receiving flask. The assembly was flushed with nitrogen and charged with trans-4-hydroxy-L-proline (100 g, 0.76 mol) and tetrahydrofuran (THF, 1.2 L), and boron trifluoride etherate (123.9 g, 0.88 mol). The mixture was heated at a rate sufficient to cause the THF to reflux gently and borane-methyl sulfide complex (360 mL, 3.6 mol) was added dropwise over 2 hrs. The solution was then refluxed for 24 hrs. The methyl sulfide, collected at stillhead was discarded, and the reaction mixture was cooled to 0° C. and quenched by the slow addition of methanol (300 mL). The reaction mixture was concentrated by distillation at reduced pressure and the residue was dissolved in 6N sodium hydroxide (1 L) and refluxed for 6 hrs. After cooling to room temperature, the insoluble material was removed by filtration and the filtrate was concentrared at reduced pressure. In order to remove the insoluble materials, the residue was dissolved in 2-propanol (1 L), filtered and concentrated. The operation was repeated three times, affording an oil, which was dissolved in 35% formaldehyde solution (200 mL) and formic acid (600 mL). The reaction mixture was refluxed for 24 hrs and concentrated at reduced pressure. The residue was dissolved in methanol (800 mL) and treated with potassium carbonate (100 g) and refluxed for 6 h. The mixture was cooled to room temperature and filtered. The filtrate was concentrated and dissolved in methylene chloride (600 mL) and filtered again. The filtrate was concentrated and Kugelrohr distilled (200°–220° C./1 mmHg) to give (2S, 4R)-4-hydroxy-1-methyl-2-pyrrolidinemethanol (54.48 g, 54.5%) as a viscous oil.

$^1$H-NMR (CDCl$_3$) δ5.14 (2H, br s), 4.25 (1H, m), 3.55 (1H, dd, J=12 and 4 Hz), 3.28 (1H, m), 2.37 (3H, s), 2.30 (1H, m), 1.72–1.99 (2H, m).

EXAMPLE 6

By the use of the procedure described above for meso-3, 4-dihydroxy-1-methylpyrrolidine, 3,4-cis-dihydroxy-1-methylpiperidine (racemic mixture) was prepared from 1,2,3, 6-tetrahydropyridine. mp. 80°–83° C.

$^1$H-NMR (CDCl$_3$) δ4.50 (1H,br s), 3.71 (1H, m), 3.58 (1H, m), 2.48–2.65 (2H, m), 2.15 (3H, s), 2.02–2.28 (2H, m), 1.74–1.85 (1H, m), 1.63–1.71 (1H, m).

EXAMPLE 7

To a solution of 35% hydrogen peroxide solution (2 mL) and formic acid (5 mL) was added 1-benzyloxycarbonyl-1, 2,3,6-tetrahydropyridine (600 mg, 2.8 mmol) which was prepared by the use of the procedure described above for meso-3,4-dihydroxy-1-methylpyrrolidine, dropwise at 0° C. and warmed to room temperature. After stirring for 24 h, the reaction mixture was concentrated to about 1 mL of volume and treated with 2N sodium hydroxide solution (10 mL) at 0° C. and further stirred at room temperature for 30 min. The mixture was extracted with chloroform (10 mL×2) and the organic layer was dried (MgSO$_4$), evaporated and purified by flash column chromatography (EtOAc/hexane (1:1)— EtOAc only) to give 3,4-trans-1-benzyloxycarbnonyl-3,4-dihydroxypiperidine (403 mg, 58%) as an oil. 3,4-trans-1-benzyloxycarbnonyl-3,4-dihydroxypiperidine (403 mg, 1.14 mmole) was converted to 3,4-trans-dihydroxy-1-methylpiperidine (174 mg, 83%) by the use of the procedure described above for meso-3,4-dihydroxy-1-methylpyrrolidine.

$^1$H-NMR(CDCl$_3$) δ5.20 (1H,br s), 3.45–3.52 (1H, m), 3.20–3.30 (1H, m), 2.82–2.90 (1H, m), 2.65–2.71 (1H, m), 2.21 (3H, s), 1.80–2.01 (2H, m), 1.50–1.61 (1H, m).

EXAMPLE 8

To a stirred solution of iodomethyl cephem (II, 100 mg, 0.29 mmol) in DMF (2 mL) was added N-methyl-bis(2-hydroxyethyl)amine (III, 104 mg, 0.87 mmol) in one portion at 20°–25° C. with stirring. After 1h, aminothiazole hydroxybezothiazole ester (IV, Q=CH, 120 mg, 0.34 mmol) was added, and the mixture was stirred. After 12 hrs, the reaction mixture was subjected to flash column chromatography on silica gel (CH$_3$CN/H$_2$O=4:1) to afford 7-[(Z)-2-(2-aminothiazol-4-yl)-2 -methoxyiminoacetamido]-3-[N-methyl-N,N-bis(2-hydroxyethyl)aminio]methyl-3-cephem-4-carboxylate (I-a, 22 mg) as powder. Yield 15%.

$^1$H NMR(D$_2$O) δ7.07 (1H, s), 5.92 (1H, d, J=4.9 Hz), 5.41 (1 H, d, J=4.9 Hz), 4.23, 4.93 (ABq, J=13.8 Hz), 4.04 (3H, s), 3.19 (3H, s). IR (KBr) 3358, 1769, 1614, 1537 cm$^{-1}$.

EXAMPLE 9

To a stirred solution of iodomethyl cephera (II, 100 mg, 0.29 mmol) in DMF (2 mL) was added N-methyl-bis(2-hydroxyethyl)amine (III, 104 mg, 0.87 mmol) in one portion at 20°–25° C. with stirring. After 1h, aminothiadiazole hydroxybezothiazole ester (IV, Q=N, 60 mg, 0.17 mmol) was added, and the mixture was stirred. After 12 hrs, the reaction mixture was subjected to flash column chromatography on silica gel (CH$_3$CN/H$_2$O=4:1) to afford 7-[(Z)-2-(5-amino-1,2,4-thiadiazol-3 -yl)-2-methoxyiminoacetamido-3-[N-methyl-N,N-bis(2-hydroxyethyl)aminio]methyl-3-cephem-4 -carboxylate (I-j, 10 mg) as powder. Yield 10%.

$^1$H NMR (D$_2$O) δ5.92 (1H, d, J=4.9 Hz), 5.41 (1H, d, J=4.9 Hz), 4.25, 4.93 (ABq, J=13.8 Hz), 4.11 (3H, s), 3.16 (3H, s). IR(KBr) 3321, 1767, 1674, 1617, 1524 cm$^{-1}$.

EXAMPLE 10

By the use of the procedure for 7-[(Z)-2-(2-aminothiazol-4-yl)-2-methoxyiminoacetamido]-3 -[N-methyl-N,N-bis(2-hydroxyethyl)aminio]methyl-3-cephem-4-carboxylate (I-a)

described above, 7-[(Z)-2-(2-aminothiazol-4-yl)-2-methoxyiminoacetamido]-3-[3,4-trans-dihydroxy-1-methylpyrrolidinio]methyl-3-cephem-4-carboxylate (I-b) was prepared from rac-3,4-trans-dihydroxy-1-methylpyrrolidine. Yield 18%.

$^1$H NMR (D$_2$O) δ7.02 (1H, s), 5.88 (1H, d, J=4.8 Hz), 5.37 (1H, J=4.8 Hz), 4.00 (3H, s), 3.22 (3H, s). IR(KBr) 3408, 1769, 1617, 1535 cm$^{-1}$.

EXAMPLE 11

By the use of the procedure for 7-[(Z)-2-(5-amino-1,2,4-thiadiazol-3-yl)-2-methoxy iminoacetamido]-3-[N-methyl-N,N-bis(2-hydroxyethyl) aminio]methyl-3-cephem-4-carboxylate (I-k) described above, 7-[(Z)-2-(5-amino-1,2,4-thiadiazol-3-yl)-2-methoxyiminoacetamido]-3-[3,4-trans-dihydroxy-1-methylpyrrolidinio]methyl-3-cephem-4-carboxylate (I-b) was prepared from rac-3,4-trans-dihydroxy-1-methylpyrrolidine. Yield 17%.

$^1$H NMR (D$_2$O) δ5.91 (1H, d, J=4.8 Hz), 5.36 (1H, d, J=4.8 Hz), 4.00 (3 H, s), 3.23 (3H, s). IR(KBr) 3410, 1769, 1617, 1526 cm$^{-1}$.

EXAMPLE 12

By the use of the procedure for 7-[(Z)-2-(2-aminothiazol-4-yl)-2-methoxyiminoacetamido]-3-[N-methyl-N,N-bis(2-hydroxyethyl)aminio]methyl-3-cephem-4-carboxylate (I-a) described above, 7-[(Z)-2-(2-aminothiazol-4-yl)-2-methoxyiminoacetamido]-3-(3S, 4S)-3,4-dihydroxy-1-methylpyrrolidinio]methyl-3-cephem-4-carboxylate (I-c) was prepared from (3S, 4S)-3,4-trans-dihydroxy-1-methylpyrrolidine.

$^1$H NMR (D$_2$O) δ7.04 (1H, s), 5.89 (1H, d, J=4.7 Hz), 5.38 (1 H, d, J=4.7 Hz), 4.02 (3H, s), 3.24, 3.27 (3H, two s). IR(KBr) 3320, 1775, 1661, 1615, 1535 cm$^{-1}$.

EXAMPLE 13

By the use of the procedure for 7-[(Z)-2-(5-amino-1,2,4-thiadiazol-3-yl)-2-methoxyiminoacetamido]-3-[N-methyl-N,N-bis(2-hydroxyethyl)aminio]methyl-3-cephem-4-carboxylate (I-b) described above, 7-[(Z)-2-(5-amino-1,2,4-thiadiazol-3-yl)-2-methoxyiminoacetamido]-3-(3S, 4S)-3,4-trans-dihydroxy-1-methylpyrrolidinio]methyl-3-cephem-4-carboxylate (I-1) was prepared from (3S, 4S)-3,4-trans-dihydroxy-1-methylpyrrolidine.

$^1$H NMR (D$_2$O) δ5.93 (1H, d, J=4.7 Hz), 5.39 (1H, d, J=4.7 Hz), 4.12 (3 H, s), 3.25, 3.28 (3H, two s). IR(KBr) 3322, 1771, 1616, 1524 cm$^{-1}$.

EXAMPLE 14

By the use of the procedure for 7-[(Z)-2-(2-aminothiazol-4-yl)-2-methoxyiminoacetamido]-3-[N-methyl-N,N-bis(2-hydroxyethyl)aminio]methyl-3-cephem-4-carboxylate (I-a) described above, 7-[(Z)-2-(2-aminothiazol-4-yl)-2-methoxyiminoacetamido]-3-[(3R, 4R)-3,4-dihydroxy-1-methylpyrrolidinio]methyl-3-cephem-4-carboxylate (I-d) was prepared from (3R, 4R)-3,4-trans-dihydroxy-1-methylpyrrolidine.

$^1$H NMR(D$_2$O) d 7.04 (1H, s), 5.89 (1H, d, J=4.7 Hz), 5.38 (1H, d, J=4.7 Hz)

EXAMPLE 15

By the use of the procedure for 7-[(Z)-2-(5-amino-1,2,4-thiadiazol-3-yl)-2-methoxyiminoacetamido]-3-[N-methyl-N,N-bis(2-hydroxyethyl) aminio]methyl-3-cephem-4-carboxylate (I-b) described above, 7-[(Z)-2-(5-amino-1,2,4-thiadiazol-3-yl)-2-methoxyiminoacetamido]-3-[(3S S,4S)-3,4-trans-dihydroxy-1-methylpyrrolidinio]methyl-3-cephem-4-carboxylate (I-m) was prepared from (3R, 4R)-3,4-trans-dihydroxy-1-methylpyrrolidine.

$^1$H NMR(D$_2$O) δ5.89 (1H, d, J=4.7 Hz), 5.36 (1H, d, J=4.7 Hz), 4.09 (3 H, s), 3.24(3H, s). IR(KBr) 3322, 1771, 1616, 1524 cm$^{-1}$

EXAMPLE 16

By the use of the procedure for 7-[(Z)-2-(2-aminothiazol-4-yl)-2-methoxyiminoacetamido]-3-[N-methyl-N,N-bis(2-hydroxyethyl)aminio]methyl-3-cephem-4-carboxylate (I-a) described above, 7-[(Z)-2-(2-aminothiazol-4-yl)-2-methoxyiminoacetamido]-3-[meso-3,4-dihydroxy-1-methylpyrrolidinio]methyl-3-cephem-4-carboxylate (I-e) was prepared from meso-3,4-dihydroxy-1-methylpyrrolidine. Yield 20%.

$^1$H NMR(D$_2$O) δ7.04 (1H, s), 5.90 (1H, d, J=4.8 Hz), 5.39 (1H, d,J=4.8 Hz)

EXAMPLE 17

By the use of the procedure for 7-[(Z)-2-(5-amino-1,2,4-thiadiazol-3-yl)-2-methoxyiminoacetamido]-3-[N-methyl-N,N-bis(2-hydroxyethyl) aminio]methyl-3-cephem-4-carboxylate (I-b) described above, 7-[(Z)-2-(5-amino-1,2,4-thiadiazol-3-yl)-2-methoxyiminoacetamido]-3-[meso-3,4-dihydroxy-1-methylpyrrolidinio]methyl-3-cephem-4-carboxylate (I-n) was prepared from meso-3,4-dihydroxy-1-methylpyrrolidine. Yield 7%.

$^1$H NMR(D$_2$O) δ5.90 (1H, d, J=4.7 Hz), 5.38 (1H, d, J=4.7 Hz), 4.10 (3 H, s), 3.27 (3H, s). IR(KBr) 3345, 1771, 1613, 1528 cm$^{-1}$

EXAMPLE 18

By the use of the procedure for 7-[(Z)-2-(2-aminothiazol-4-yl)-2-methoxyiminoacetamido]-3-[N-methyl-N,N-bis(2-hydroxyethyl)aminio]methyl-3-cephem-4-carboxylate (I-a) described above, 7-[(Z)-2-(2-aminothiazol-4-yl)-2-methoxyiminoacetamido]-3-[(4 R)-hydroxy-(2S)-hydroxymethyl-1-methylpyrrolidinio]methyl-3-cephem-4-carboxylate(I-f) was prepared from (2S, 4R)-4-hydroxy-1-methyl-2-pyrrolidinemethanol. Yield 16%.

$^1$H NMR(D$_2$O) δ7.02 (1H, s), 5.87 (1H, d, J=4.7 Hz), 5.38 (1 H, d, J=4.7 Hz), 4.00 (3H, s), 3.17 (3H, s). IR(KBr) 3320, 1771, 1617, 1535 cm$^{-1}$

EXAMPLE 19

By the use of the procedure for 7-[(Z)-2-(5-amino-1,2,4-thiadiazol-3-yl)-2-methoxyiminoacetamido]-3-[N-methyl-N,N-bis(2-hydroxyethyl)aminio]methyl-3-cephem-4-carboxylate (I-b) described above, 7-[(Z)-2-(5-amino-1,2,4-thiadiazol-3-yl)-2-methoxyiminoacetamido]-3-[(4R)-hydroxy-(2S)-hydroxymethyl-1-methylpyrrolidinio]-methyl-3-cephem-4-carboxylate (I-o) was prepared from (2S, 4R)-4-hydroxy-1-methyl-2pyrrolidinemethanol. Yield 10%.

¹H NMR (D₂O) δ7.01 (1H, s), 5.87 (1H, d, J=4.7 Hz), 5.37 (1 H, d, J=4.7 Hz), 3.99 (3H, s), 3.06, 3.19 (3H, two s), 2.10 (2H, m). IR(KBr) 3322, 1771, 1618, 1537 cm⁻¹

EXAMPLE 20

By the use of the procedure for 7-[(Z)-2-(2-aminothiazol-4-yl)-2-methoxyiminoacetamido]-3 -[N-methyl-N,N-bis(2-hydroxyethyl)aminio]methyl-3-cephem-4-carboxylate (I-a) described above, 7-[(Z)-2-(2-aminothiazol-4-yl)-2-methoxyiminoacetamido]-3-[3,4 -cis-dihydroxy-1-methylpiperidinio]methyl-3-cephem-4-carboxylate (I-g) was prepared from 3,4-cis-dihydroxy-1-methylpiperidine. Yield 14%.

¹H NMR (D₂O) δ7.01 (1H, s), 5.87 (1H, d, J=4.7 Hz), 5.37 (1 H, d, J=4.7 Hz), 3.99 (3H, s), 3.06, 3.19 (3H, two s), 2.10 (2H, m). IR(KBr) 3322, 1771, 1618, 1537 cm⁻¹

EXAMPLE 21

By the use of the procedure for 7-[(Z)-2-(5-amino-1,2,4-thiadiazol-3-yl)-2 -methoxyiminoacetamido]-3-[N-methyl-N,N-bis(2-hydroxyethyl)aminio]methyl-3-cephem-4-carboxylate (I-b) described above, 7-[(Z)-2-(5-amino-1,2,4-thiadiazol-3-yl)-2-methoxyiminoacetamido]-3 -[3,4-cis-dihydroxy-1-methylpiperidinio]methyl-3-cephem-4-carboxylate (I-p) was prepared from 3,4-cis-dihydroxy-1-methylpiperidine. Yield 21%.

¹H NMR (D₂O) δ5.91 (1H, d, J=4.9 Hz), 5.40 (1H, d, J=4.9 Hz), 4.07 (3 H, s), 3.35, 3.98 (2H, ABq, J=13.3 Hz), 3.06, 3.19 (3H, two s), 2.10 (2H, m). IR(KBr) 3320, 1771, 1617, 1524 cm⁻¹

EXAMPLE 22

By the use of the procedure for 7-[(Z)-2-(2-aminothiazol-4-yl)-2-methoxyiminoacetamido]-3 -[N-methyl-N,N-bis(2-hydroxyethyl)aminio]methyl-3-cephem-4-carboxylate (I-a) described above, 7-[(Z)-2-(2-aminothiazol-4-yl)-2-methoxyiminoacetamido]-3-[3,4 -trans-dihydroxy-1-methylpiperidinio]methyl-3-cephem-4-carboxylate (I-h) was prepared from 3,4-trans-dihydroxy-1-methylpiperidine. Yield 20%.

¹H NMR(D₂O) δ7.04 (1H, s), 5.90 (1H, d, J=4.8 Hz), 5.40 (1 H, d, J=4.8 Hz), 4.02 (3H, s), 3.13, 3.19 (3H, two s). IR(KBr) 3387, 1771, 1615, 1526 cm⁻¹

EXAMPLE 23

By the use of the procedure for 7-[(Z)-2-(5-amino-1,2,4-thiadiazol-3-yl)-2 -methoxyiminoacetamido]-3-[N-methyl-N,N-bis(2-hydroxyethyl)aminio]methyl-3-cephem-4-carboxylate (I-b) described above, 7-[(Z)-2-(5-amino-1,2,4-thiadiazol-3-yl)-2-methoxyiminoacetamido]-3 -[3,4-trans-dihydroxy-1-methylpiperidinio]methyl-3-cephem-4-carboxylate (I-q) was prepared from 3,4-trans-dihydroxy-1-methylpiperidine. Yield 9%.

¹H NMR(D₂O) δ5.94 (1H, d, J=4.9 Hz), 5.41 (1H, d, J=4.9 Hz), 4.10 (3 H, s), 3.19(3H, s). IR(KBr) 3312, 1773, 1615, 1534 cm⁻¹

EXAMPLE 24

By the use of the procedure for 7-[(Z)-2-(2-aminothiazol-4-yl)-2-methoxyimino-acetamido]-3 -tropiniomethyl-3-cephem-4-carboxylate (I-a) described above, 7-[(Z)-2-(2-aminothiazol-4-yl)-2-methoxyiminoacetamido]-3 -tropinio]methyl-3-cephem-4-carboxylate (I-i) was prepared from tropine. Yield 14%.

¹H NMR (D₂O) δ7.02 (1H, s), 5.87 (1H, d, J=4.8 Hz), 5.35 (1 H, d, J=4.8 Hz), 4.00 (3H, s), 2.93, 3.00 (3H, two s). IR(KBr) 3368, 1765, 1617, 1534 cm⁻¹

EXAMPLE 25

By the use of the procedure for 7-[(Z)-2-(5-amino-1,2,4-thiadiazol-3-yl)-2 -methoxyiminoacetamido]-3-[N-methyl-N,N-bis(2-hydroxyethyl)aminio]methyl-3-cephem-4-carboxylate (I-b) described above, 7-[(Z)-2-(5-amino-1,2,4-thiadiazol-3-yl)-2-methoxyiminoacetamido]-3 -tropiniomethyl-3-cephem-4-carboxylate (I-r) was prepared from tropine. Yield 18%.

¹H NMR (D₂O) δ5.89 (1H, d, J=4.7 Hz), 5.36 (1H, d, J=4.6 Hz), 4.09 (3 H, s), 2.92, 3.00 (3H, two s). IR(KBr) 3412, 1773, 1672, 1617, 1526 cm⁻¹

We claimed:

1. Quaternary ammonium cephalosporins with hydroxylated alicyclic or aliphatic amines represented as formula (I);

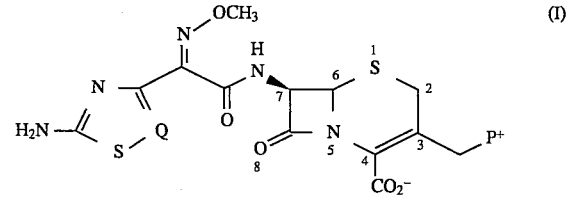

wherein Q is CH or N and P is selected from the group consisting of N-methyl-bis(2-hydroxyethyl)amine, rac-3,4-trans-dihydroxy-1-methylpyrrolidine, (3S, 4S)-3,4-dihydroxy-1-methylpyrrolidine, (3R, 4R)-3,4-dihydroxy-1-methylpyrrolidine, meso-3,4-dihydroxy-1-methylpyrrolidine, (2S,4R)-4-hydroxyl-1-methyl-2-pyrrolidinemethanol, 3,4,-cis-dihydroxy-1-methylpiperidine,3,4-trans-dihydroxy-1-methylpiperidine and tropine.

2. Quaternary ammonium cephalosporins according to claim 1 wherein the Q is CH.

3. Quaternary ammonium cephalosporins according to claim 1 wherein the Q is N.

* * * * *